United States Patent

Henning et al.

Patent Number: 4,525,301
Date of Patent: Jun. 25, 1985

[54] PROCESS FOR THE PREPARATION OF N-ALKYLATED DIPEPTIDES AND THEIR ESTERS

[75] Inventors: Rainer Henning, Hattersheim am Main; Hansjörg Urbach, Kronberg, both of Fed. Rep. of Germany

[73] Assignee: Hoechst Aktiengesellschaft, Frankfurt, Fed. Rep. of Germany

[21] Appl. No.: 604,220

[22] Filed: Apr. 26, 1984

[30] Foreign Application Priority Data

Apr. 28, 1983 [DE] Fed. Rep. of Germany ....... 3315464

[51] Int. Cl.³ .......................................... C07C 103/52
[52] U.S. Cl. .......................................... 260/112.5 R
[58] Field of Search ................................ 260/112.5 R

[56] References Cited

FOREIGN PATENT DOCUMENTS 3317290 11/1983 Fed. Rep. of Germany .

*Primary Examiner*—Delbert R. Phillips
*Attorney, Agent, or Firm*—Finnegan, Henderson, Farabow, Garrett & Dunner

[57] ABSTRACT

The invention relates to a process for the preparation of compounds of the formula I

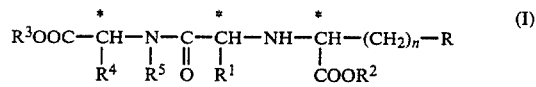

in which n is 1 or 2, R represents hydrogen, an aliphatic, cycloaliphatic, aromatic, araliphatic, cycloaliphatic-aliphatic radical or a radical $OR^a$ or $SR^2$, in which $R^a$ denotes alkyl, aryl or heteroaryl, $R^1$ denotes hydrogen, an aliphatic, cycloaliphatic-aliphatic, aromatic, araliphatic, heteroaromatic radical or an aminoacid side chain, $R^2$ and $R^3$ are identical or different and denote hydrogen, an aliphatic, cycloaliphatic, aromatic or araliphatic radical, and $R^4 + R^5$, together with the atoms carrying them, form a heterocyclic ring system, which comprises reacting trifluoromethanesulfonic acid derivatives of the formulae II or III with aminoacid esters of the formulae IV or V respectively. The invention also relates to compounds of the formula III and a process for their preparation.

14 Claims, No Drawings

PROCESS FOR THE PREPARATION OF N-ALKYLATED DIPEPTIDES AND THEIR ESTERS

The invention relates to a process for the preparation of compounds of the formula I

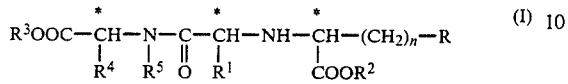

in which n is 1 or 2,

R denotes hydrogen, an optionally substituted aliphatic radical having 1 to 8 carbon atoms, an optionally substituted cycloaliphatic radical having 3–9 carbon atoms, an optionally substituted aromatic radical having 6–12 carbon atoms, an optionally substituted araliphatic radical having 7–14 carbon atoms, an optionally substituted cycloaliphatic-aliphatic radical having 7–14 carbon atoms, or a radical $OR^a$ or $SR^a$, in which $R^a$ represents an optionally substituted aliphatic radical having 1–4 carbon atoms, an optionally substituted aromatic radical having 6–12 carbon atoms or an optionally substituted heteroaromatic radical having 5–12 ring atoms, $R^1$ denotes hydrogen, an optionally substituted aliphatic radical having 1 to 6 carbon atoms, an optionally substituted cycloaliphatic radical having 3–9 carbon atoms, an optionally substituted cycloaliphatic-aliphatic radical having 4–13 carbon atoms, an optionally substituted aromatic radical having 6–12 carbon atoms, an optionally substituted araliphatic radical having 7–16 carbon atoms, an optionally substituted heteroaromatic radical having 5–12 ring atoms or the side-chain of an optionally protected naturally occurring α-aminoacid, $R^2$ and $R^3$ are identical or different and denote hydrogen, an optionally substituted aliphatic radical having 1–6 carbon atoms, an optionally substituted cycloaliphatic radical having 3–9 carbon atoms, an optionally substituted aromatic radical having 6–12 carbon atoms, an optionally substituted araliphatic radical having 7–16 carbon atoms, and $R^4$ and $R^5$, together with the atoms carrying them, form a monocyclic, bicyclic or tricyclic heterocyclic ring system having 5 to 15 carbon atoms.

Particularly suitable ring systems of this type are those in the group below: pyrrolidine (A); piperidine (B); tetrahydroisoquinoline (C); decahydroisoquinoline (D); octahydroindole (E); octahydrocyclopenta[b]pyrrole (F); 2-azabicyclo[2.2.2]octane (G); 2-azabicyclo[2.2.1]heptane (H); 2-azaspiro[4.5]decane (I); 2-azaspiro[4.4]nonane (J); spiro[(bicyclo[2.2.1]heptane)-2,3-pyrrolidine] (K); spiro[(bicyclo[2.2.2]octane)-2,3-pyrrolidine] (L); 2-azatricyclo[4.3.0.1^{6,9}]decane (M); decahydrocyclohepta[b]pyrrole (N); octahydroisoindole (O); octahydrocyclopenta[c]pyrrole (P); 2,3,3,a,4,5,7a-hexahydroindole (Q); and tetrahydrothiazole (R); which can all optionally be substituted. However, the unsubstituted systems are preferred.

The suitable cyclic aminoacid esters have the structural formulae below:

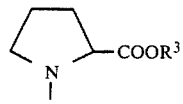 A

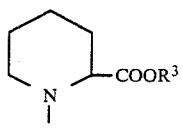 B

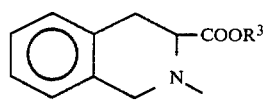 C

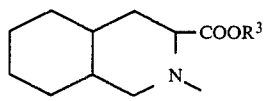 D

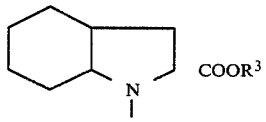 E

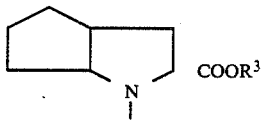 F

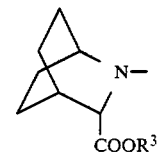 G

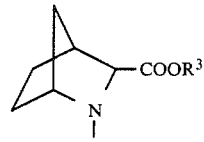 H

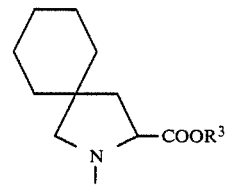 I

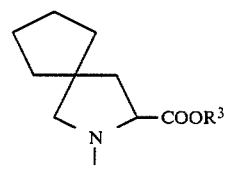 J

-continued

K
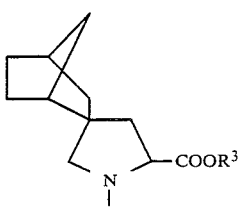

L
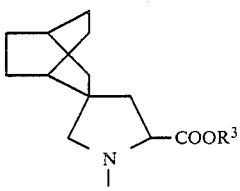

M
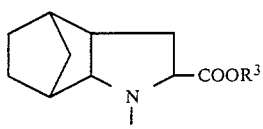

N
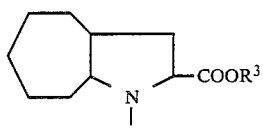

O
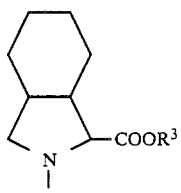

P
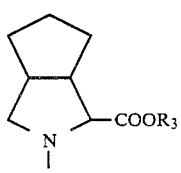

Q
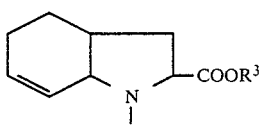

R
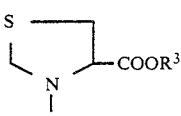

The process comprises reacting compounds of formulae II and III

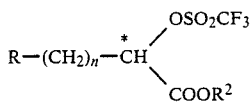 (II)

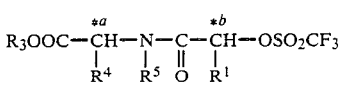 (III)

in which n, R, $R^1$, $R^2$, $R^3$ and $R^4$ and $R^5$ have the above-mentioned meanings, with compounds of the formulae IV and V respectively

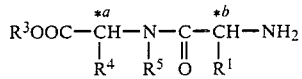 (IV)

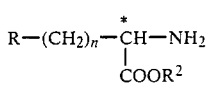 (V)

in which n, R, $R^1$, $R^2$, $R^3$, $R^4$ and $R^5$ have the above-mentioned meanings, splitting off, where appropriate, ester groups by hydrolysis or hydrogenolysis and, where appropriate, esterifying free carboxyl groups in a manner known per se.

Processes for the preparation of compounds of the formula I by reaction of α-halogenocarboxylic esters or the corresponding tosyloxy or mesyloxy compounds with aminoacid esters or dipeptide esters by nucleophilic substitution are known from the literature (for example from U.S. Pat. No. 4,350,704 and European Pat. Nos. A 49,605 and 46,953). In general, these reactions require an elevated reaction temperature, and the yields are frequently low by reason of the drastic reaction conditions which favor side reactions. Catalysis with silver ions, such as, for example, in the reaction of the α-halogenocarboxylic esters, is frequently necessary, and this improves the yield but makes the process considerably more costly. Racemic products are frequently obtained when optically active α-halogeno-, α-mesyloxy- or α-tosyloxy-carboxylic esters are used.

In another process known from the literature, to which the German Patent Application No. P 32 26 768.1, inter alia, relates, α-ketoesters are reacted with aminoacid esters and dipeptide esters to give the corresponding Schiff's bases and the latter are reduced with a variety of reducing agents. Sodium cyanoborohydride is particularly suitable for this. On working this up, hydrogen cyanide is produced, which makes the process very elaborate. The claimed process does not have the disadvantages indicated.

A preferred embodiment comprises preparing compounds of the formula I in which n is 1 or 2, R denotes hydrogen, alkyl having 1–8 carbon atoms, alkenyl having 2–6 carbon atoms, cycloalkyl having 3–9 carbon atoms, aryl having 6–12 carbon atoms which can be monosubstituted, disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-acylamino, preferably $(C_1-C_4)$-alkanoylamino, methylenedioxy, carboxyl, cyano and/or sulfamoyl, or alkoxy having 1–4 carbon atoms or aryloxy having 6–12 carbon atoms which can be substituted as described above for aryl, or monocyclic or bicyclic heteroaryloxy having 5–7 or 8–10 ring atoms respectively, 1 to 2 of these ring atoms being sulfur or oxygen atoms and/or 1 to 4 of these ring atoms being nitrogen, which can be substituted as described above for aryl, amino-($C_1$-$C_4$)-alkyl, ($C_1$-$C_4$)-alkanoylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl-($C_1$-$C_4$)-alkylamino-($C_1$-$C_4$)-alkyl, ($C_1$-$C_4$)-alkylamino-($C_1$-$C_4$)-alkyl, di-($C_1$-$C_4$)-alkylamino-($C_1$-$C_4$)-alkyl, guanidino-($C_1$-$C_4$)-alkyl, imidazolyl, indolyl, ($C_1$-$C_4$)-alkylthio, ($C_1$-$C_4$)-alkylthio-($C_1$-$C_4$)-alkyl, ($C_6$-$C_{12}$)-arylthio-($C_1$-$C_4$)-alkyl, which can be substituted in the aryl moiety as described above for aryl, ($C_6$-$C_{12}$)-aryl-($C_1$-$C_4$)-alkylthio, which can be substituted in the aryl moiety as described above for aryl, carboxyl-($C_1$-$C_4$)-alkyl, carboxyl, carbamoyl, carbamoyl-($C_1$-$C_4$)-alkyl, ($C_1$-$C_4$)-alkoxycarbonyl-($C_1$-$C_4$)-alkyl, ($C_6$-$C_{12}$)-aryloxy-($C_1$-$C_4$)-alkyl, which can be substituted in the aryl moiety as described above for aryl, or ($C_6$-$C_{12}$)-aryl-($C_1$-$C_4$)-alkoxy, which can be substituted in the aryl moiety as described above for aryl, $R^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, ($C_3$-$C_9$)-cycloalkyl-($C_1$-$C_4$)-alkyl, ($C_5$-$C_9$)-cycloalkenyl-($C_1$-$C_4$)-alkyl, optionally partially hydrogenated aryl having 6-12 carbon atoms which can be substituted as described above for R, ($C_6$-$C_{12}$)-aryl-($C_1$-$C_4$)-alkyl or ($C_7$-$C_{13}$)-aroyl-($C_1$ or $C_2$)-alkyl, both of which can be substituted as the previous aryl, monocyclic or bicyclic, optionally partially hydrogenated, heteroaryl having 5-7 or 8-10 ring atoms respectively, 1 or 2 of these ring atoms being sulfur or oxygen atoms and/or 1 to 4 of these ring atoms being nitrogen atoms, which can be substituted as the previous aryl, or the side chain of an optionally protected naturally occurring α-aminoacid $R^1$—CH(NH$_2$)—COOH, $R^2$ and $R^3$ are identical or different and denote hydrogen, alkyl having 1-6 carbon atoms, alkenyl having 2-6 carbon atoms, di-($C_1$-$C_4$)-alkylamino-($C_1$-$C_4$)-alkyl, ($C_1$-$C_5$)-alkanoyloxy-($C_1$-$C_4$)-alkyl, ($C_1$-$C_6$)-alkoxycarbonyloxy-($C_1$-$C_4$)-alkyl, ($C_7$-$C_{13}$)-aroyloxy-($C_1$-$C_4$)-alkyl, ($C_6$-$C_{12}$)-aryloxycarbonyloxy-($C_1$-$C_4$)-alkyl, aryl having 6-12 carbon atoms, ($C_6$-$C_{12}$)-aryl-($C_1$-$C_4$)-alkyl, ($C_3$-$C_9$)-cycloalkyl or ($C_3$-$C_9$)-cycloalkyl-($C_1$-$C_4$)-alkyl, and $R^4$ and $R^5$ have the meanings indicated above.

That embodiment is particularly preferred which comprises preparing compounds of the formula I in which n is 1 or 2, R denotes ($C_1$ to $C_6$)-alkyl, ($C_2$ to $C_6$)-alkenyl, ($C_3$ to $C_9$)-cycloalkyl, amino-($C_1$-$C_4$)-alkyl, ($C_2$-$C_5$)-acylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$ to $C_{12}$)-aryl-($C_1$-$C_4$)-alkoxycarbonylamino-($C_1$-$C_4$)-alkyl, ($C_6$ to $C_{12}$)-aryl which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl, especially methyl, ethyl, cyclohexyl, tert.-butoxycarbonylamino-($C_1$-$C_4$)-alkyl, benzoyloxycarbonylamino-($C_1$-$C_4$)-alkyl or phenyl which can be monosubstituted or disubstituted or, in the case of methoxy, trisubstituted by phenyl, ($C_1$ or $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro and/or methylenedioxy, $R^1$ denotes hydrogen or ($C_1$ to $C_6$)-alkyl which can optionally be substituted by amino, ($C_1$ to $C_6$)-acylamino or benzoylamino, ($C_2$ to $C_6$)-alkenyl, ($C_3$ to $C_9$)-cycloalkyl, ($C_5$ to $C_9$)-cycloalkenyl, ($C_3$ to $C_7$)-cycloalkyl-($C_1$ to $C_4$)-alkyl, ($C_6$ to $C_{12}$)-aryl or partially hydrogenated aryl, each of which can be substituted by ($C_1$ to $C_4$)-alkyl, ($C_1$ or $C_2$)-alkoxy or halogen, ($C_6$-$C_{12}$)-aryl-($C_1$ to $C_4$)-alkyl or ($C_7$-$C_{13}$)-aroyl-($C_1$-$C_2$)-alkyl, both of which can be substituted in the aroyl radical as previously defined, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, or a side chain of a naturally occurring, optionally protected, α-aminoacid, but particularly hydrogen, ($C_1$ to $C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$ denote identical or different radicals hydrogen, ($C_1$ to $C_6$)-alkyl, ($C_2$ to $C_6$)-alkenyl or ($C_6$ to $C_{12}$)-aryl-($C_1$ to $C_4$)-alkyl, but especially hydrogen, ($C_1$ to $C_4$)-alkyl or benzyl, and $R^4$ and $R^5$ have the meanings indicated above.

In this context and in the following, aryl is understood preferably to include optionally substituted phenyl, biphenylyl or naphthyl. This is correspondingly true of radicals derived from aryl, such as aryloxy and arylthio. Aroyl is particularly understood to include benzoyl. Aliphatic radicals can be straight-chain or branched.

A monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, is understood to include, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Naturally occurring α-aminoacids are described, for example, in Houben-Weyl, Methoden der Organischen Chemie (Methods of Organic Chemistry), Volumes XV/1 and XV/2.

When $R^1$ represents a side chain of a protected, naturally occurring α-aminoacid, such as, for example, protected Ser, Thr, Asp, Asn, Glu, Gln, Arg, Lys, Hyl, Cys, Orn, Cit, Tyr, Trp, His or Hyp, the preferred protective groups are those customary in peptide chemistry (cf. Houben-Weyl, Volumes XV/1 and XV/2). In the case where $R^1$ denotes the protected side chain of lysine, the known amino protective groups, but particularly Z, Boc or ($C_1$-$C_6$)-alkanoyl, are preferred, Preferred O-protective groups suitable for tyrosine are ($C_1$-$C_6$)-alkyl, especially methyl or ethyl.

Using the process according to the invention, compounds of the formula I can be obtained in which the center of chirality produced in this $S_N2$ reaction is in the S or R configuration or is racemic, depending on which chiral starting compounds have been used.

The reaction taking place in the process according to the invention takes an unambiguous stereochemical course. This fact is also verified by investigations of the stereochemical course of the reaction of α-trifluoromethanesulfonyloxy-carboxylic esters with optically active amines (Effenberger et al., Angew. Chem. 95 (1983) 50).

The diagram below illustrates the stereochemical course of the reaction in the process according to the invention:

Starting compounds——>

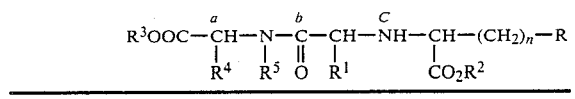

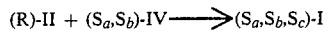

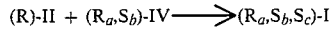

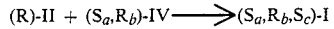

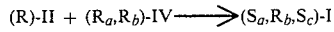

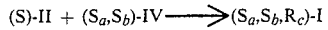

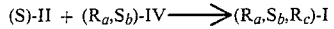

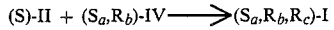

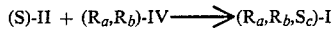

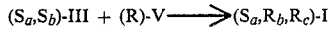

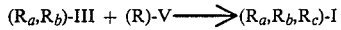

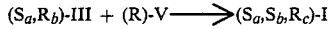

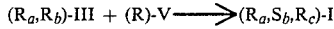

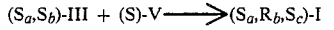

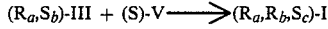

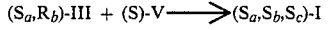

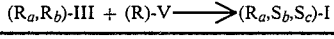

The compounds below can be obtained particularly advantageously using the process according to the invention: N-(1-S-carboethoxy-3-phenylpropyl)-S-alanyl-S-proline benzyl ester, N-(1-R-carboethoxy-3-phenylpropyl)-S-alanyl-S-proline benzyl ester, N-(1-R,S-carboethoxy-3-phenylpropyl)-S-alanyl-S-proline benzyl ester, N-(1-S-carboethoxy-3-cyclohexylpropyl)-S-alanyl-S-proline benzyl ester, N-(1-R-carboethoxy-3-cyclohexylpropyl)-S-alanyl S-proline benzyl ester, N-(1-R,S-carboethoxy-3-cyclohexylpropyl)-S-alanyl-S-proline benzyl ester, N-(1-S-carboethoxy-3-phenylpropyl)-N$_\epsilon$-benzyloxycarbonyl-S-lysyl-S-proline tert.-butyl ester, N-(1-S-carboethoxy-3-phenylpropyl)-S-tyrosyl-S-proline benzyl ester, N-(1-S-carboethoxy-3-phenylpropyl)-O-methyl-S-tyrosyl-S-proline benzyl ester, N-(1-S-carboethoxy-3-phenylpropyl)-O-ethyl-S-tyrosyl-S-proline benzyl ester, benzyl N-(1-S-carboethoxy-3-phenylpropyl)-S-alanyl-S-pipecolate, benzyl N-(1-S-carboethoxy-3-cyclohexylpropyl)-S-alanyl-S-pipecolate, tert.-butyl N-(1-S-carboethoxy-3-phenylpropyl)-S-alanyl-S-1,2,3,4-tetrahydroisoquinoline-3-carboxylate, tert.-butyl N-(1-S-carboethoxy-3-cyclohexylpropyl)-S-alanyl-S-1,2,3,4-tetrahydroisoquinoline-3-carboxylate, tert.-butyl N-(1-S-carboethoxy-3-phenylpropyl)-N$_\epsilon$-benzylcarbonyl-S-lysyl-S-1,2,3,4-tetrahydroisoquinoline-3-carboxylate, tert.-butyl N-(1-carboethoxy-3-phenylpropyl)-O-ethyl-S-tyrosyl-S-1,2,3,4-tetrahydroisoquinoline-3-carboxylate, benzyl N-(1-S-carboethoxy-3-phenylpropyl)-S-alanyl-3S-decahydroisoquinoline-3-carboxylate, benzyl N-(1-S-carboethoxy-3-phenylpropyl)-S-alanyl-(2S, 3aS,7aS)-octahydroindole-2-carboxylate, benzyl N-(1-S-carboethoxy-3-cyclohexylpropyl)-S-alanyl-(2S,3aS,7aS)-octahydroindole-2-carboxylate, tert.-butyl N-(1-S-carboethoxy-3-phenylpropyl)-N$_\epsilon$-benzyloxycarbonyl-S-lysyl-(2S,3aS,7aS)-octahydroindole-2-carboxylate, tert.-butyl N-(1-S-carboethoxy-3-cyclohexylpropyl)-N$_\epsilon$-benzyloxycarbonyl-S-lysyl-(2S,3aS,7aS)-octahydroindole-2-carboxylate, benzyl N-(1-S-carboethoxy-3-phenylpropyl)-O-methyl-S-tyrosyl-(2S,3aS,7aS)-octahydroindole-2-carboxylate, benzyl N-(1-S-carboethoxy-3-phenylpropyl)-O-ethyl-S-tyrosyl-(2S,3aS,7aS)-octahydroindole-2-carboxylate, benzyl N-(1-S-carboethoxy-4,4-dimethylphenyl)-S-alanyl-(2S,3aS,7aS)-octahydroindole-2-carboxylate, benzyl N-[1-S-carboethoxy-3-(4-fluorophenyl)-propyl]-S-alanyl-(2S,3aS,7aS)-octahydroindole-2-carboxylate, benzyl N-[1-S-carboethoxy-3-(4-methoxyphenyl)-propyl]-S-alanyl-(2S,3aS,7aS)-octahydroindole-2-carboxylate, benzyl N-[1-S-carboethoxy-3-(3,4-dimethoxyphenyl)-propyl]-S-alanyl-(2S,3aS,7aS)-octahydroindole-2-carboxylate, benzyl N-(1-S-carboethoxy-3-cyclopentylpropyl)-S-alanyl-(2S,3aS,7aS)-octahydroindole-2-carboxylate, benzyl N-(1-S-carboethoxy-3-phenylpropyl)-S-alanyl-(2S,3aR,7aS)-octahydroindole-2-carboxylate, benzyl N-(1-S-carboethoxy-3-cyclohexylpropyl)-S-alanyl-(2S,3aR,7aS)-octahydroindole-2-carboxylate, tert.-butyl N-(1-S-carboethoxy-3-phenylpropyl)-N$_\epsilon$-benzyloxycarbonyl-S-lysyl-(2S,3aR,7aS)-octahydroindole-2-carboxylate, benzyl N-(1-S-carboethoxy-3-cyclohexylpropyl)-N$_\epsilon$-benzyloxycarbonyl-S-lysyl-(2S,3aR,7aS)-octahydroindole-2-carboxylate, benzyl N-(1-S-carboethoxy-3-phenylpropyl)-O-ethyl-S-tyrosyl-(2S,3aR,7aS)-octahydroindole-2-carboxylate, benzyl N-(1-S-carboethoxy-3-phenylpropyl)-S-alanyl-(2S,3aR,7aR)-octahydroindole-2-carboxylate, tert.-butyl N-(1-S-carboethoxy-3-phenylpropyl)-N$_\epsilon$-benzyloxycarbonyl-S-lysyl-(2S,3aR,7aR)-octahydroindole-2-carboxylate, benzyl N-(1-S-carboethoxy-3-cyclohexylpropyl)-S-alanyl-(2S,3aR,7aR)-octahydroindole-2-carboxylate, benzyl N-(1-S-carboethoxy-3-cyclohexylpropyl)-O-ethyl-S-tyrosyl-(2S,3aR,7aR)-octahydroindole-2-carboxylate, benzyl N-(1-S-carboethoxy-3-phenylpropyl)-S-alanyl-(2S,3aS,7aR)-octahydroindole-2-carboxylate, benzyl N-(1-S-carboethoxy-3-phenylpropyl)-S-alanyl-(2S,3aS,6aS)-octahydrocyclopenta[b]pyrrole-2-carboxylate, benzyl N-(1-S-carboethoxy-3-cyclohexylpropyl)-S-alanyl-(2S,3aS,6aS)-octahydrocyclopenta[b]pyrrole-2-carboxylate, tert.-butyl N-(1-S-carboethoxy-3-phenylpropyl)-N$_\epsilon$-benzylcarboxycarbonyl-S-lysyl-(2S,3aS,6aS)-octahydrocyclopenta[b]pyrrole-2-carboxylate, tert.-butyl N-(1-S-carboethoxy-3-cyclohexylpropyl)-N$_\epsilon$-benzyloxycarbonyl-S-lysyl-(2S,3aS,6aS)-octahydrocyclopenta[b]pyrrole-2-carboxylate, benzyl N-(1-S- carboethoxy-3-phenylpropyl)-O-methyl-S-tyrosyl-(2S,3aS,6aS)-octahydrocyclopenta[b]pyrrole-2-carboxylate, benzyl N-(1-S-carboethoxy-3-phenylpropyl)-O-ethyl-S-tyrosyl-(2S,3aS,6aS)-octahydrocyclopenta[b]pyrrole-2-carboxylate, benzyl N-(1-S-carboethoxy-3-[4-fluorophenyl]-propyl)-S-alanyl-(2S,3aS,6aS)-octahydrocyclopenta[b]pyrrole-2-carboxylate, benzyl N-(1-S-carboethoxy-3-[4-methoxyphenyl]-propyl)-S-alanyl-(2S,3aS,6aS)-octahydrocyclopenta[b]pyrrole-2-carboxylate, benzyl N-(1-S-carboethoxy-3-cyclopentylpropyl)-S-alanyl-(2S,3aS,6aS)-octahydrocyclopenta[b]pyrrole-2-carboxylate, benzyl N-(1-S-carboethoxy-3-phenylpropyl)-S-alanyl-(2S,3aR,6aR)-octahydrocyclopenta[b]pyrrole-2-carboxylate, benzyl N-(1-S-carboethoxy-3-cyclohexylpropyl)-S-alanyl-(2S,3aR,6aR)-octahydrocyclopenta[b]pyrrole-2-carboxylate, tert.-benzyl N-(1-S-carboethoxy-3-phenylpropyl)-N$_\epsilon$-benzyloxycarbonyl-S-lysyl-(2S,3AR,6aR)-octahydrocyclopenta[b]pyrrole-2-carboxylate, benzyl N-(1-S-carboethoxy-3-phenylpropyl)-S-alanyl-(2S,3aR,6aS)-octahydrocyclopenta[b]pyrrole-2-carboxylate, benzyl N-(1-S-carboethoxy-3-cyclohexylpropyl)-S-alanyl-(2S,3aR,6aS)-octahydrocyclopenta[b]pyrrole-2-carboxylate, tert.-butyL N-(1-S-carboethoxy-3-phenylpropyl)-N$_\epsilon$-benzyloxycarbonyl-S-lysyl-(2S,3aR,6aS)-octahydrocyclopenta[b]pyrrole-2-carboxylate, tert.-butyl N-(1-S-carboethoxy-3-cyclohexylpropyl)-N$_\epsilon$-benzyloxycarbonyl-S-lysyl-(2S,3aR,6aS)-octahydrocyclopenta[b]pyrrole-2-carboxylate, benzyl N-(1-S-carboethoxy-3-phenylpropyl)-O-ethyl-S-tyrosyl-(2S,3aR,6aS)-octahydrocyclopenta[b]pyrrole-2-carboxylate, benzyl N-(1-S-carboethoxy-3-cyclopentylpropyl)-S-alanyl-2-(2S,3aR,6aS)-octahydrocyclopenta[b]pyrrole-2-carboxylate, benzyl N-(1-S-carboethoxy-3-phenylpropyl)-S-alanyl-S-2-azabicyclo[2.2.2]octane-3-carboxylate, benzyl N-(1-S-carboethoxy-3-phenylpropyl)-O-ethyl-S-tyrosyl-S-2-azabicyclo[2.2.2]octane-3-carboxylate, benzyl N-(1-S-carboethoxy-3-cyclohexylpropyl)-S-alanyl-S-2-azabicyclo[2.2.2]octane-3-carboxylate, tert.-butyl N-(1-S-carboethoxy-3-cyclohexylpropyl)-N$_\epsilon$-benzyloxycarbonyl-S-2-azabicyclo[2.2.2]octane-3-carboxylate, tert.-butyl N-(1-S-carboethoxy-3-phenylpropyl)-N$_\epsilon$-benzyloxycarbonyl-S-lysyl-S-2-azabicyclo-[2.2.2]octane-3-carboxylate, benzyl N-(1-S-carboethoxy-3-cyclopentylpropyl)-S-alanyl-S-2-azabicyclo[2.2.2]octane-3-carboxylate, benzyl N-(1-S-carboethoxy-3-phenylpropyl)-S-alanyl-3S-exo-2-azabicyclo[2.2.1]heptane-3-carboxylate, benzyl N-(1-S-carboethoxy-3-cyclohexylpropyl)-S-alanyl-3S-exo-2-azabicyclo[2.2.1]heptane-3-carboxylate, tert.-butyl N-(1-S-carboethoxy-3-phenylpropyl)-N$_\epsilon$-benzyloxycarbonyl-S-lysyl-3S-exo-2-azabicyclo[2.2.1]heptane-3-carboxylate, benzyl N-(1-S-carboethoxy-3-phenylpropyl)-S-alanyl-3S-endo-2-azabicyclo[2.2.1]heptane-3-carboxylate, benzyl N-(1-S-carboethoxy-3-cyclohexylpropyl)-S-alanyl-3S-endo-2-azabicyclo[2.2.1]heptane-3-carboxylate, tert.-butyl N-(1-S-carboethoxy-3-phenylpropyl)-N$_\epsilon$-benzyloxycarbonyl-S-lysyl-3S-endo-2-azabicyclo[2.2.1]heptane-3-carboxylate, benzyl N-(1-S-carboethoxy-3-phenylpropyl)-O-ethyl-S-tyrosyl-3S-endo-2-azabicyclo-[2.2.1]-heptane-3-carboxylate, benzyl N-(1-S-carboethoxy-3-phenylpropyl)-S-alanyl-2-azaspiro[4,5]decane-3-S-carboxylate, benzyl N-(1-S-carboethoxy-3-phenylpropyl)-O-ethyl-S-tyrosyl-2-azaspiro[4,5]decane-3-S-carboxylate, tert.-butyl N-(1-S-carboethoxy-3-phenylpropyl)-N$_\epsilon$-benzyloxycarbonyl-S-lysyl-2-azaspiro[4,5]-decane-3-S-carboxylate, benzyl N-(1-S-carboethoxy-3-cyclohexylpropyl)-S-alanyl-2-azaspiro[4,5]decane-3-S-carboxylate, tert.-butyl N-(1-S-carboethoxy-3-cyclohexylpropyl)-N$_\epsilon$-benzyloxycarbonyl-S-lysyl-2-azaspiro[4,5]decane-3-S-carboxylate, benzyl N-(1-S-carboethoxy-3-phenylpropyl)-S-alanyl-2-azaspiro[4,4]nonane-3-S-carboxylate, benzyl N-(1-S-carboethoxy-3-phenylpropyl)-O-ethyl-S-tyrosyl-2-azaspiro[4,4]nonane-3-S-carboxylate, benzyl N-(1-S-carboethoxy-3-phenylpropyl)-N$_\epsilon$-tert.-butoxycarbonyl-S-lysyl-2-azaspiro[4,4]nonane-3-S-carboxylate, benzyl N-(1-S-carboethoxy-3-cyclohexylpropyl)-S-alanyl-2-azaspiro[4,4]nonane-3-S-carboxylate, benzyl N-(1-S-carboethoxy-3-cyclopentylpropyl)-S-alanyl-2-azaspiro[4,4]nonane-3-S-carboxylate, benzyl N-(1-S-carboethoxy-3-cyclopentylpropyl)-N$_\epsilon$-tert.-butoxycarbonyl-S-lysyl-2-azaspiro[4,4]nonane-3-S-carboxylate, benzyl N-(1-S-carboethoxy-3-phenylpropyl)-S-alanyl-spiro[bicyclo[2.2.1]heptane-2,3'-pyrrolidine]-5'-S-carboxylate, benzyl N-(1-S-carboethoxy-3-phenylpropyl)-O-ethyl-S-tyrosyl-spiro]bicyclo[2.2.1]heptane-2,3'-pyrrolidine]-5'-S-carboxylate, tert.-butyl N-(1-S-carboethoxy-3-phenylpropyl)-N$_\epsilon$-benzyloxycarbonyl-S-lysyl-spiro[bicyclo[2.2.1]heptane-2,3'-pyrrolidine]-5'-S-carboxylate, benzyl N-(1-S-carboethoxy-3-cyclohexylpropyl)-S-alanyl-spiro[bicyclo[2.2.1]heptane-2,3'-pyrrolidine]-5'-S-carboxylate, benzyl N-(1-S-carboethoxy-3-cyclohexylpropyl)-N$_\epsilon$-tert.-butoxycarbonyl-S-lysyl-spiro[bicyclo[2.2.1]heptane-2,3'-pyrrolidine]-5'-S-carboxylate, benzyl N-(1-S-carboethoxy-3-phenylpropyl)-S-alanyl-spiro]bicyclo[2.2.2]octane-2,3'-pyrrolidine]-5'-S-carboxylate, benzyl N-(1-S-carboethoxy-3-phenylpropyl)-O-ethyl-S-tyrosyl-spiro]bicyclo[2.2.2]octane-2,3'-pyrrolidine]-5'-S-carboxylate, benzyl N-(1-S-carboethoxy-3-phenylpropyl)-N$_\epsilon$-tert.-butoxycarbonyl-S-lysyl-spiro]bicyclo[2.2.2]octane-2,3'-pyrrolidine]-5'-S-carboxylate, benzyl N-(1-S-carboethoxy-3-cyclohexylpropyl)-S-alanyl-spiro[bicyclo[2.2.2]octane-2,3'-pyrrolidine]-5'-S-carboxylate, benzyl N-(1-S-carboethoxy-3-phenylpropyl)-S-alanyl-azatricyclo[4.3.0.1$^{6,9}$]decane-3-S-carboxylate, benzyl N-(1-S-carboethoxy-3-phenylpropyl)-O-ethyl-S-tyrosyl-2-azatricyclo[4.3.0.1$^{6,9}$]decane-3-S-carboxylate, tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate, benzyl N-(1-S-carboethoxy-3-cyclohexylpropyl)-S-alanyl-2-azatricyclo[4.3.0.1$^{6,9}$]-decane-3-S-carboxylate, tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate, benzyl N-(1-S-carboethoxy-3-phenylpropyl)-S-alanyl-decahydrocyclohepta[b]pyrrole-2-S-carboxylate, benzyl N-(1-S-carboethoxy-3-phenylpropyl)-O-ethyl-S-tyrosyl-decahydrocyclohepta[b]pyrrole-2-S-carboxylate, tert.-butyl N-(1-S-carboethoxy-3-phenylpropyl)-N$_\epsilon$-benzyloxycarbonyl-S-lysyl-decahydrocyclohepta[b]pyrrole-2-S-carboxylate, benzyl N-(1-S-carboethoxy-3-cyclohexylpropyl)-S-alanyl-decahydrocyclohepta[b]pyrrole-2-S-carboxylate, benzyl N-(1-S-carboethoxy-3-cyclohexylpropyl)-N$_\epsilon$-tert.butoxycarbonyl-S-lysyl-decahydrocyclohepta[b]pyrrole-2-S-carboxylate, benzyl N-(1-S-carboethoxy-3-phenylpropyl)-S-alanyl-transoctahydroisoindole-1-S-carboxylate, benzyl N-(1-S-carboethoxy-3-phenylpropyl)-S-alanyl-cis-octahydroisoindole-1-S-carboxylate, benzyl N-(1-S-carboethoxy-3-cyclohexylpropyl)-S-alanyl-trans-octahydroisoindole-1-S-carboxylate, benzyl N-(1-S-carboethoxy-3-cyclohexylpropyl)-S-alanyl-cis-octahydroisoindole-1-S-carboxylate, benzyl N-(1-S-carboethoxy-3-phenylpropyl)-S-alanyl-cis-octahydrocyclopenta[c]pyrrole-1-S-carboxylate, benzyl N-(1-S-carboethoxy-3-cyclohexylpropyl)-S-alanyl-cis-octahydrocyclopenta[c]pyrrole-1-S-carboxylate, benzyl N-(1-S-carboethoxy-3-cyclohexylpropyl)-N$_\epsilon$-tert.-butoxycarbonyl-S-lysyl-cis-octahydrocyclopenta[c]pyrrole-1-S-carboxylate, tert.-butyl N-(1-S-carboethoxy-3-phenylpropyl)-S-alanyl-2,3,3a,4,5,7a-hexahydroindole-2-S-carboxylate, tert.-butyl N-(1-S-carboethoxy-3-cyclohexylpropyl)-O-ethyl-S-tyrosyl-2,3,3a,4,5,7a-hexahydroindole-2-S-carboxylate, tert.-butyl N-(1-S-carboethoxy-3-cyclohexylpropyl)-S-alanyl-2,3,3a,4,5,7a-hexahydroindole-2-S-carboxylate, tert.-butyl N-(1-S-carboethoxy-3-phenylpropyl)-S-alanyl-thiazolidine-5-S-carboxylate, tert.butyl N-(1-S-carboethoxy-3-cyclohexylpropyl)-S-alanyl-thiazolidine-5-S-carboxylate, tert.-butyl N-(1-S-carboethoxy-3-phenylpropyl)-N$_\epsilon$-benzyloxycarbonyl-lysyl-thiazolidine-5-S-carboxylate.

The invention also relates to compounds of the formula III in which $R^1$ denotes hydrogen or ($C_1$ to $C_6$)-alkyl which can optionally be substituted by amino, ($C_1$ to $C_6$)-acylamino, preferably Boc- or ($C_1$–$C_6$)-alkanoylamino, or benzoylamino, ($C_2$ to $C_6$)-alkenyl, ($C_3$ to $C_9$)-cycloalkyl, ($C_5$ to $C_9$)-cycloalkenyl, ($C_3$ to $C_7$)-cycloalkyl-($C_1$ to $C_4$)-alkyl, ($C_6$ to $C_{12}$)-aryl or partially hydrogenated aryl, each of which can be substituted by ($C_1$ to $C_4$)-alkyl, ($C_1$ or $C_2$)-alkoxy or halogen, ($C_6$ to $C_{12}$)-aryl-($C_1$ to $C_4$)-alkyl or ($C_7$ to $C_{13}$)-aroyl-($C_1$–$C_2$)-alkyl, both of which can be substituted in the aryl radical as previously defined, a monocyclic or bicyclic heterocyclic radical having 5 to 7 or 8 or 10 ring atoms respectively, 1 to 2 of these ring atoms being sulfur or oxygen atoms and/or 1 to 4 of these ring atoms being nitrogen atoms, or a side chain of a naturally occurring optionally protected, α-aminoacid, $R_3$ denotes hydrogen, ($C_1$ to $C_6$)-alkyl, ($C_2$ to $C_6$)-alkenyl or ($C_6$–$C_{12}$)-aryl-($C_1$ to $C_4$)-alkyl, and $R^4$ and $R^5$ have the meanings indicated for compounds of the formula I.

Those compounds of the formula III are preferred in which $R^1$ denotes hydrogen, ($C_1$ to $C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^3$ denotes hydrogen, ($C_1$ to $C_4$)-alkyl or benzyl, and $R^4$ and $R^5$ have the meanings indicated for compounds of the formula I, but especially compounds of the formula III in which $R^1$ denotes methyl, ethyl, phenyl, the optionally acylated side chain of lysine, benzyl or the ($C_1$–$C_6$)-O-alkylated side chain of tyrosine, $R^3$ denotes hydrogen, methyl, ethyl, tert.-butyl or benzyl and $R^4$ and $R^5$ have the meanings indicated for compounds of the formula I.

The trifluoromethanesulfonates of the formulae II and III are obtained by reacting α-hydroxycarboxylic acid derivatives of the formulae VI and VII respectively

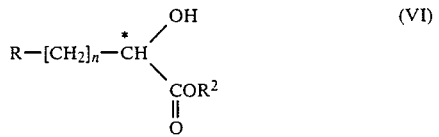

(VI)

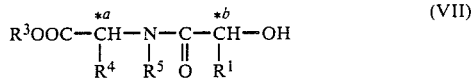

(VII)

in which, n, R, $R^1$, $R^2$, $R^3$, $R^4$ and $R^5$ have the above-mentioned meanings, with a trifluoromethanesulfonating agent, such as, for example, trifluoromethanesulfonic anhydride or trifluoromethanesulfonyl chloride, in an inert solvent.

The dipeptide derivatives of the formula IV and the hydroxycarboxamides of the formula VII are obtained by methods known per se in peptide chemistry, using suitable protective group techniques, from the corresponding aminoacids or hydroxyacids.

It is advantageous to carry out the reaction in the presence of a base in order to capture the acid produced in the reaction. Inorganic salts, such as carbonates (for example $K_2CO_3$, $Na_2CO_3$, $NaHCO_3$) or $Na_2SO_4$, or organic bases, such as, for example, triethylamine or pyridine are suitable for this. The base can be used in the stoichiometric amount or in excess.

Suitable solvents are those which cannot react with the trifluoromethanesulfonating agent and the trifluoromethanesulfonyl derivatives. Examples of these are solvents such as methylene chloride, chloroform, carbon tetrachloride or other halogenated hydrocarbons, or hydrocarbons, such as, for example, hexane. The reaction can be carried out in the range of temperature between −80° C. and +80° C. The reaction in methylene chloride, chloroform or carbon tetrachloride is particularly advantageous, trifluoromethanesulfonic anhydride being reacted with the α-hydroxycarboxylic acid derivative in the presence of pyridine at temperatures between −80° C. and room temperature. It is also possible to use trifluoromethanesulfonic anhydride in excess.

When optically active compounds of the formulae VI or VII are employed, the configuration at the chiral carbon atom is retained on conversion into the compounds of the formulae II or III.

The trifluoromethanesulfonyl derivatives of the formulae II and III react smoothly with aminoacid esters of the formulae IV and V respectively to give compounds of the formula I. In order to capture the trifluoromethanesulfonic acid which is produced, the reaction is advantageously carried out in the presence of one equivalent of a base which cannot react with compounds of the formulae II or III. tert.-Amines, such as triethylamine or pyridine, have proved to be advantageous. It is also possible for the aminoacid derivatives themselves to act as the acid-capture agent. Inorganic salts, such as, for example, $Na_2CO_3$, $K_2CO_3$, $NaHCO_3$ and $Na_2SO_4$ are also suitable.

The reaction is carried out in an aprotic polar solvent or non-polar solvent. Examples of suitable solvents are methylene chloride, chloroform, carbon tetrachloride, dimethylformamide, ethyl acetate, dimethoxyethane, hexane, ether and tetrahydrofuran.

The reaction temperature is in the range between −80° and +150° C. −20° to +80° C. has proved to be particularly advantageous.

Working-up is very straightforward. The solvent is washed with water in order to remove the salts which are formed. The organic solution is dried and evaporated, whereupon the pure compounds of the formula I are obtained, it being possible for them to be highly purified, where necessary, using the general methods of purification, such as, for example, filtration or chromatography on silica gel, inter alia.

When optically pure compounds of the formulae II or III are employed in the reaction, then the substitution of the trifluoromethanesulfonic ester by the amino-acid derivatives of the formula IV or V takes place with inversion of configuration. Optically pure final products are obtained from optically pure starting materials with no racemization. A mixture of diastereomers is obtained when, for example, racemic compounds of the formula II or III are reacted with optically pure aminoacid derivatives or vice versa, or racemic compounds of the formula II or III are reacted with racemic aminoacid derivatives. The diastereomers produced can be separated using the generally customary methods of separation, such as, for example, fractional crystallization of the salts or column chromatography on silica gel, inter alia. Even when one of the starting components is racemic, the process according to the invention has great advantages compared with known processes because of its high yields and purity.

The compounds of the formula I are inhibitors of angiotensin converting enzyme (ACE) or are intermediates in the preparation of inhibitors of this type, and can be employed for controlling high blood pressure of various etiologies. Compounds of this type are known, for example, from U.S. Pat. No. 4,350,633, U.S. Pat. No. 4,344,949, U.S. Pat. No. 4,294,832, U.S. Pat. No. 4,350,704, European Pat. No. A 50,800, European Pat. No. A 31,741, European Pat. No. A 51,020, European Pat. No. A 49,658, European Pat. No. A 49,605, European Pat. No. A 29,488, European Pat. No. A 46,953 and European Pat. No. A 52,870. The German Patent Applications Nos. P 32 26 768.1, P 31 51 690.4, P 32 10 496.0, P 32 11 397.8, P 32 11 676.4, P 32 27 055.0, P 32 42 151.6, P 32 46 503.3 and P 32 46 757.5 also relate to them.

The examples which follow are intended to illustrate the process according to the invention without restricting the invention to the substances which are mentioned here as representative.

EXAMPLE 1 tert.-Butyl N-(1-carboethoxy-3-phenylpropyl)-S-alanyl-1,2,3,4-tetrahydroisoquinoline-3-S-carboxylate (Diastereomers A 1 and B 1)

1.62 g (3.4 millimoles) of the p-toluenesulfonate of tert.-butyl S-alanyl-1,2,3,4-tetrahydroisoquinoline-3-S-carboxylate are dissolved in 50 ml of 10% strength sodium carbonate solution and extracted three times with dichloromethane; the extract is dried with sodium sulfate and evaporated. The residue, together with 3.4 millimoles of triethylamine, is dissolved in 10 moles of dry dichloromethane; 1.16 g (3.4 millimoles) of ethyl 4-phenyl-2-R,S-trifluoromethanesulfonyloxybutyrate, dissolved in 5 ml of dry dichloromethane, is added dropwise at 20° C. After 1 hour at 20° C., the mixture is washed with water, dried over sodium sulfate and evaporated. The diastereomers A 1 and B 1 are separated by chromatography on silica gel using ethyl acetate/cyclohexane (1:2) as the mobile phase.

Diastereomer A 1: 0.57 g (35% yield)

| $^1$H-NMR data (CDCl$_3$): | 7.15 | (s, 9H) |
|---|---|---|
| | 5.5 − 5.2 | (m, 1H) |
| | 4.6 | (s, 2H) |
| | 4.4 − 3.5 | (m, 4H) |
| | 3.4 − 1.6 | (m, 6H) |
| | 1.4 − 1.05 | (d + t, 6H) |
| | 1.25 | (s, 9H) ppm |
| Diastereomer B 1: 0.51 g (31% yield) | | |
| $^1$H-NMR data (CDCl$_3$): | 7.2 | (s, 9H) |
| | 5.45 − 5.0 | (2dd, 1H) |
| | 4.71 + 4.65 | (2s, 2H) |
| | 4.4 − 3.5 | (m, 4H) |
| | 3.3 − 1.6 | (m, 6H) |
| | 1.5 − 1.1 | (d + t, 6H) |
| | 1.27 | (s, 9H) ppm. |

The required ethyl 2-R,S-trifluoromethanesulfonyloxy-4-phenylbutyrate is obtained by adding a solution of 2.37 g of pyridine and 9.73 g of trifluoromethanesulfonic anhydride in 8 ml of dichloromethane dropwise to a solution of 6.24 g (30 millimoles) of ethyl 2-R,S-hydroxy-4-phenylbutyrate in 30 ml of dry dichloromethane, with stirring at 0° C., within one hour, and stirring a further 15 minutes at 0° C., filtering off the precipitate with suction, evaporating the filtrate and filtering through silica gel. 8.6 g of the ester are obtained. Rf value: 0.37 (SiO$_2$, cyclohexane/ethyl acetate 4:1).

EXAMPLE 2 tert.-Butyl N-(1-S-carboethoxy-3-phenylpropyl)-S-alanyl-1,2,3,4-tetrahydroisoquinoline-3-S-carboxylate (a) Ethyl 2-R-trifluoromethanesulfonyloxy-4-phenylbutyrate The compound is obtained from ethyl 2-R-hydroxy-4-phenylbutyrate and trifluoromethanesulfonic anhydride in analogy to the procedure for preparation in Example 1. The ethyl ester is prepared from 2-R-hydroxy-4-phenylbutyric acid (Biquard, Annales de Chimie 20, page 145 (1933)) and absolute ethanol by passing dry hydrogen chloride gas into the solution warmed on a waterbath, in analogy to the procedure or Biquard, Annales de Chimie 20, 147 (1933).

Rf: 0.11 (SiO$_2$, cyclohexane/ethyl acetate 9:1)

Yield: 90%

(b) tert.-Butyl N-(1-S-carboethoxy-3-phenylpropyl)-S-alanyl-1,2,3,4-tetrahydroisoquinoline-3-S-carboxylate Ethyl 2-R-trifluoromethanesulfonyloxy-4-phenylbutyrate is reacted with tert.-butyl S-alanyl-1,2,3,4-tetrahydroisoquinoline-3-S-carboxylate in analogy to Example 1. The desired S,S,S-compound is obtained in 84% yield via inversion of configuration in the butyric acid moiety. The physical data are identical with those of diastereomer B 1, Example 1.

EXAMPLE 3

N-(1-S-Carboethoxy-3-phenylpropyl)-O-methyl-S-tyrosyl-S-proline benzyl ester

Prepared from ethyl 2-R-trifluoromethanesulfonyloxy-4-phenylbutyrate and O-methyl-S-tyrosyl-S-proline benzyl ester by the process described in Example 2b.

m/e: 572.

EXAMPLE 4

Benzyl N-(1-S-carboethoxy-3-phenylpropyl)-O-ethyl-S-tyrosyl-(2S,3aS,7aS)-octahydroindole-2-carboxylate Prepared from ethyl 2-R-trifluoromethanesulfonyloxy-4-phenylbutyrate and benzyl O-ethyl-S-tyrosyl-(2S,3aS,7aS)-octahydroindole-2-carboxylate by the process described in Example 2b.

m/e: 640

EXAMPLE 5 tert.-Butyl N-(1-S-carboethoxy-3-phenylpropyl)-N$_\epsilon$-benzyloxycarbonyl-S-lysyl-(2S,3aS,6aS)-octahydrocyclopenta[b]pyrrole-2S-carboxylate Prepared from ethyl 2-R-trifluoromethanesulfonyloxy-4-phenylbutyrate and tert.-butyl N$_\epsilon$-benzyloxycarbonyl-S-lysyl-(2S,3aS,6aS)-octahydrocyclopenta[b]pyrrole-2-carboxylate in analogy to the process described in Example 2b.

m/e: 663

EXAMPLE 6

Benzyl N-(1-S-carboethoxy-3-cyclohexylpropyl)-S-alanyl-(2S,3aS,6aS)-octahydrocyclopenta[b]pyrrole-2-carboxylate (a) Ethyl 2-R-trifluoromethanesulfonyloxy-4-cyclohexylbutyrate Prepared from ethyl 2-R-hydroxy-4-cyclohexylbutyrate by the procedure described in Example 2a.

$^1$H-NMR data (CDCl$_3$) $\delta$=5.05 (t, 1H), 4.25 (q, 2H), 2.3–0.9 (m, 15H), 1.3 (t, 3H) ppm.

(b) Benzyl N-(1-S-carboethoxy-3-cyclohexylpropyl)-S-alanyl-(2S,3aS,6aS)-octahydrocyclopenta[b]pyrrole-2-carboxylate Prepared from ethyl 2-R-trifluoromethanesulfonyloxy-4-cyclohexylbutyrate and benzyl S-alanyl-(2S,3aS,6aS)-octahydrocyclopenta[b]pyrrole-2-carboxylate by the process described in Example 2b.

$^1$H-NMR data (CDCl$_3$) $\delta$=7.33, (s, 5H), 5.15, (s, 2H), 4.65, (dd, 1H), 4.2, (q, 2H), 3.8–1.0, (m, 27H), 1.3, (t, 3H) ppm.

EXAMPLE 7

Benzyl N-(1-S-carboethoxy-3-cyclohexylpropyl)-S-alanyl-(2S,3aS,7aS)-octahydroindole-2-carboxylate Prepared from ethyl 2-R-trifluoromethanesulfonyloxy-4-cyclohexylbutyrate and benzyl S-alanyl-(2S,3aS,7aS)-octahydroindole-2-carboxylate by the process indicated in Example 2b.

$^1$H-NMR data (CDCl$_3$): $\delta$=7.3, (s, 5H), 5.1, (AB system, 2H), 4.6–1.0, (m, 30H), 1.3, (t, 3H) ppm.

EXAMPLE 8

Benzyl N-(1-S-carboethoxy-3-phenylpropyl)-S-alanyl-(2S,3aS,6aS)-octahydrocyclopenta[b]pyrrole-2-carboxylate (a) Benzyl N-(2-R-trifluoromethanesulfonyloxypropionyl-(2S,3aS,6aS)-octahydrocyclopenta[b]pyrrole-2-carboxylate A solution of 0.8 g of dry pyridine and 3.25 g of trifluoromethanesulfonic anhydride in 5 ml of dry dichloromethane is added dropwise, with stirring at 0° C., to a solution of 3.03 g (10 millimoles) of benzyl N-(2-R-hydroxypropionyl)-(2S,3aS,6aS)-octahydrocyclopenta[b]pyrrole-2-carboxylate (prepared from benzyl (2S,3aS,6aS)-octahydrocyclopenta[b]pyrrole-2-carboxylate and tetrahydropyranyl lactate in the presence of dicyclohexylcarbodiimide/1-hydroxybenzotriazole and subsequent acid catalyzed hydrolysis of the tetrahydropyranyl group) in 10 ml of dry dichloromethane.

After 15 minutes at 0° C., the precipitate is filtered off, the filtrate is evaporated and purified on silica gel using cyclohexane/ethyl acetate (4:1) as the mobile phase.

Yield: 76%.

(b) Benzyl N-(1-S-carboethoxy-3-phenylpropyl)-S-alanyl-(2S,3aS,6aS)-octahydrocyclopenta[b]pyrrole-2-carboxylate 3.3 g (7.6 millimoles) of the compound from Example 8a are stirred at 25° C. for 8 hours with 1.57 g (7.6 millimoles) of S-homophenylalanine ethyl ester and 0.5 ml of triethylamine in 20 ml of dichloromethane, and the mixture is evaporaed and purified on silica gel using cyclohexane/ethyl acetate (1:1) as the mobile phase.

m/e: 486.

Yield: 67%.

Furthermore, using the processes indicated in Example 1, 2a and 8a, starting from the appropriate 2-hydroxycarboxylic esters, which are employed in the R or S or R,S form, preferably the R or R,S form, or from the appropriate hydroxyacylamino acid esters which have the R or S or R,S, preferably the R or R,S, configuration at the carbon atoms bearing the hydroxyl group, the following trifluoromethanesulfonates are prepared. Ethyl 2-R,S-trifluoromethanesulfonyloxy-5,5-dimethylhexanoate, ethyl 2-R-trifluoromethanesulfonyloxy-5,5-dimethylhexanoate, ethyl 2-R,S-trifluoromethanesulfonyloxy-4-cyclopentylbutyrate, ethyl 2-R-trifluoromethanesulfonyloxy-4-cyclopentylbutyrate, ethyl 2-R,S-trifluoromethanesulfonyloxy-4-(4-fluorophenyl)butyrate, ethyl 2-R-trifluoromethanesulfonyloxy-4-(4-fluorophenyl)butyrate, ethyl 2-R,S-trifluoromethanesulfonyloxy-4-(4-methoxyphenyl)butyrate, ethyl 2-R-trifluoromethanesulfonyloxy-4-(4-methoxyphenyl)butyrate, ethyl 2-R,S-trifluoromethanesulfonyloxy-4-(3,4-methoxyphenyl)butyrate, ethyl 2-R-trifluoromethanesulfonyloxy-4-(3,4-methoxyphenyl)butyrate, N-(2-R,S-trifluoromethanesulfonyloxypropionyl)-S-proline benzyl ester, N-2-R-trifluoromethanesulfonyloxypropionyl)-S-proline benzyl ester, N-[2-R,S-trifluoromethanesulfonyloxypropionyl]-3-(4-ethoxyphenyl)propionyl]-S-proline benzyl ester, tert.-butyl N-(2-R,S-trifluoromethanesulfonyloxypropionyl)-1,2,3,4-tetrahydroisoquinoline-3-S-carboxylate, tert.-butyl N-(2-R-trifluoromethanesulfonyloxypropionyl)-1,2,3,4-tetrahydroisoquinoline-3-S-carboxylate, benzyl N-(2-R-trifluoromethanesulfonyloxypropionyl)decahydroisoquinoline-3-S-carboxylate, benzyl N-(2-R-trifluoromethanesulfonyloxypropionyl)-(2S,3aS,7aS)-octahydroindole-2-carboxylate, benzyl N-(2-R-trifluoromethanesulfonyloxypropionyl)-(2S,3aR,7aS)-octahydroindole-2-carboxylate, benzyl N-(2-R-trifluoromethanesulfonyloxypropionyl)-(2S,3aR,7aR)-octahydroindole-2-carboxylate, benzyl N-(2-R-trifluoromethanesulfonyloxypropionyl)-(2S,3aS,7aR)-octahydroindole-2-carboxylate, benzyl N-(2-R-trifluoromethanesulfonyloxypropionyl)-(2S,3aR,6aR)-octahydrocyclopenta[b]pyrrole-2-carboxylate, benzyl N-(2-R-trifluoromethanesulfonyloxypropionyl)-(2S,3aR,6aR)-octahydrocyclopenta[b]pyrrole-2-carboxylate, benzyl N-(2-R-trifluoromethanesulfonyloxypropionyl)-2-azabicyclo[2.2.2]octane-3-S-carboxylate, benzyl N-(2-R-trifluoromethanesulfonyloxypropionyl)-exo-2-azabicyclo-[2.2.1]heptane-3-S-carboxylate, benzyl N-(2-R-trifluoromethanesulfonyloxypropionyl)-endo-2-azabicyclo[2.2.1]-heptane-3-S-carboxylate, benzyl N-(2-R-trifluoromethanesulfonyloxypropionyl)-2-azaspiro[4.5]decane-3-S-carboxylate, benzyl N-(2-R-trifluoromethanesulfonyloxypropionyl)-2-azaspiro[4.4-]nonane-3-S-carboxylate, benzyl N-(2-R-trifluoromethanesulfonyloxypropionyl)-spiro[bicyclo-[2.2.2]octane-2,3'-pyrrolidine]-5'-S-carboxylate, benzyl N-(2-R-trifluoromethanesulfonyloxypropionyl)-spiro[bicyclo[2.2.1]heptane-2,3'-pyrrolidine]-5'-S-carboxylate, benzyl N-(2-R-trifluoromethanesulfonyloxypropionyl)-2-azatricyclo[4.3.0.1$^{6,9}$]decane-3-S-carboxylate, benzyl N-(2-R-trifluoromethanesulfonyloxypropionyl)-decahydrocyclohepta[b]pyrrole-2-S-carboxylate, benzyl N-(2-R-trifluoromethanesulfonyloxypropionyl)-cis-octahydroisoindole-1-S-carboxylate, benzyl N-(2-R-trifluoromethanesulfonyloxypropionyl)-trans-octahydroisoindole-1-S-carboxylate, benzyl N-(2-R-trifluoromethanesulfonyloxypropionyl)-cis-octahydrocyclopenta[c]pyrrole-1-S-carboxylate, tert.-butyl N-(2-R-trifluoromethanesulfonyloxypropionyl)-2,3,3a,4,5,7a-hexahydroindole-2-S-carboxylate, tert.-butyl N-(2-R-trifluoromethanesulfonyloxypropionyl)thiazolidine-5-S-carboxylate.

The 2-R,S-hydroxycarboxylic esters necessary for the preparation of the trifluoromethanesulfonates are obtained from the corresponding α-keto esters by reduction with Raney nickel and hydrogen. Another process for their preparation comprises subjecting the appropriate cyanohydrins to acid hydrolysis and esterifying the hydroxycarboxylic acids by conventional esterification processes.

The 2-R- and 2-R,S-hydroxyacylamino acid esters are obtained from the corresponding aminoacid esters and suitably protected hydroxy acids by conventional methods of amide formation and subsequent reduction of the α-ketoacylamino acid esters obtained with sodium hydride.

Resolution of the racemic 2-hydroxycarboxylic acids takes place either via the formation of diastereomeric salts with optically active amines or aminoacid esters and fractional crystallization or by esterification with optically active alcohols, such as, for example, menthol, which can be separated by column chromatography or by fractional crystallization. The esterification to give the diastereomeric 2-hydroxycarboxylic esters takes place by customary methods of esterification.

The 2-trifluoromethanesulfonyloxycarboxylic esters described above are reacted with the appropriate dipeptide esters using the process described in Examples 1 and 2b, or the 2-trifluoromethanesulfonyloxyacylamino-acid esters are reacted with the appropriate aminoacid esters using the process described in Example 8b, to give the compounds below:

N-(1-S-Carboethoxy-3-phenylpropyl)-S-alanyl-S-proline benzyl ester, N-(1-R-carboethoxy-3-phenylpropyl)-S-alanyl-S-proline benzyl ester, N-(1-R,S-carboethoxy-3-phenylpropyl)-S-alanyl-S-proline benzyl ester, N-(1-S-carboethoxy-3-cyclohexylpropyl)-S-alanyl-S-proline benzyl ester, N-(1-R-carboethoxy-3-cyclohexylpropyl)-S-alanyl-S-proline benzyl ester, N-(1-S-carboethoxy-3-phenylpropyl)-N$_\epsilon$-benzyloxycarbonyl-S-lysyl-S-proline tert.-butyl ester, N-(1-S-carboethoxy-3-phenylpropyl)-S-tyrosyl-S-proline benzyl ester, N-(1-S-carboethoxy-3-phenylpropyl)-O-methyl-S-tyrosyl-S-proline benzyl ester, N-(1-S-carboethoxy-3-phenylpropyl)-S-alanyl-S-pipecolate, N-(1-S-carboethoxy-3-cyclohexylpropyl)-S-alanyl-S-pipecolate, tert.-butyl N-(1-S-carboethoxy-3-cyclohexylpropyl)-S-alanyl-S-1,2,3,4-tetrahydroisoquinoline-3-carboxylate, tert.-butyl N-(1-S-carboethoxy-3-phenylpropyl)-N$_\epsilon$-benzyloxycarbonyl-S-lysyl-S-1,2,3,4-tetrahydroisoquinoline-3-carboxylate, tert.-butyl N-(1-S-carboethoxy-3-phenylpropyl)-O-ethyl-S-tyrosyl-S-1,2,3,4-tetrahydroisoquinoline-3-carboxylate, benzyl N-(1-S-carboethoxy-3-phenylpropyl)-S-alanyl-3S-decahydroisoquinoline-3-carboxylate, benzyl N-(1-S-carboethoxy-3-phenylpropyl)-S-alanyl-(2S,3aS,7aS)-octahydroindole-2-carboxylate, tert.-butyl N-(1-S-carboethoxy-3-phenylpropyl)-N$_\epsilon$-benzyloxycarbonyl-S-lysyl-(2S,3aS,7aS)-octahydroindole-2-carboxylate, tert.-butyl N-(1-S-carboethoxy-3-cyclohexylpropyl)-N$_\epsilon$-benzyloxycarbonyl-S-lysyl-(2S,3aS,7aS)-octahydroindole-2-carboxylate, benzyl N-(1-S-carboethoxy-3-phenylpropyl)-O-methyl-S-tyrosyl-(2S,3aS,7aS)-octahydroindole-2-carboxylate, benzyl N-(1-S-carboethoxy-4,4-dimethylpentyl)-S-alanyl-(2S,3aS,7aS)-octahydroindole-2-carboxylate, benzyl N-[1-S-carboethoxy-3-(4-fluorophenyl)propyl]-S-alanyl-(2S,3aS,7aS)-octahydroindole-2-carboxylate, benzyl N-[1-S-carboethoxy-3-(4-methoxyphenyl)-propyl]-S-alanyl-(2S,3aS,7aS)-octahydroindole-2-carboxylate, benzyl N-[1-S-carboethoxy-3-(3,4-dimethoxyphenyl)-propyl]-S-alanyl-(2S,3aS,7aS)-octahydroindole-2-carboxylate, benzyl N-[1-S-carboethoxy-3-(cyclopentylpropyl]-S-alanyl-(2S,3aS,7aS)-octahydroindole-2-carboxylate, benzyl N-(1-S-carboethoxy-3-phenylpropyl)-S-alanyl-(2S,3aR,7aS)-octahydroindole-2-carboxylate, benzyl N-(1-S-carboethoxy-3-cyclohexylpropyl)-S-alanyl-(2S,3aR,7aS)-octahydroindole-2-carboxylate, tert.-butyl N-(1-S-carboethoxy-3-phenylpropyl)-N$_\epsilon$-benzyloxycarbonyl-S-lysyl-(2S,3aR,7aS)-octahydroindole-2-carboxylate, benzyl N-(1-S-carboethoxy-3-cyclohexylpropyl)-N$_\epsilon$-benzyloxycarbonyl-S-lysyl-(2S,3aR,7aS)-octahydroindole-2-carboxylate, benzyl N-(1-S-carboethoxy-3-phenylpropyl)-O-ethyl-S-tyrosyl-(2S,3aR,7aS)-octahydroindole-2-carboxylate, benzyl N-(1-S-carboethoxy-3-phenylpropyl)-S-alanyl-(2S,3aR,7aR)-octahydroindole-2-carboxylate, tert.-butyl N-(1-S-carboethoxy-3-phenylpropyl)-N$_\epsilon$-benzyloxycarbonyl-S-lysyl-(2S,3aS,7aR)-octahydroindole-2-carboxylate, benzyl N-(1-S-carboethoxy-3-cyclohexylpropyl)-S-alanyl-(2S,3aR,7aR)-octahydroindole-2-carboxylate, benzyl N-(1-S-carboethoxy-3-phenylpropyl)-S-alanyl-(2S,3aS,7aR)-octahydroindole-2-carboxylate, benzyl N-(1-S-carboethoxy-3-phenylpropyl)-S-alanyl-(2S,3aS,6aS)-octahydrocyclopenta[b]pyrrole-2-carboxylate, tert.-butyl N-(1-S-carboethoxy-3-cyclohexylpropyl)-N$_\epsilon$-benzyloxycarbonyl-S-lysyl- (2S,3aS,6aS)-octahydrocyclopenta[b]pyrrole-2-carboxylate, benzyl N-(1-S-carboethoxy-3-phenylpropyl)-O-methyl-S-tyrosyl-(2S,3aS,6aS)-octahydrocyclopenta[b]pyrrole-2-carboxylate, benzyl N-(1-S-carboethoxy-3-phenylpropyl)-O-ethyl-S-tyrosyl-(2S,3aS,6aS)-octahydrocyclopenta[b]pyrrole-2-carboxylate, benzyl N-(1-S-carboethoxy-3-[4-fluorophenyl]-propyl)-S-alanyl-(2S,3aS,6aS)-octahydrocyclopenta[b]pyrrole-2-carboxylate, benzyl N-(1-S-carboethoxy-3-[4-methoxyphenyl]-propyl)-S-alanyl-(2S,3aS,6aS)-octahydrocyclopenta[b]pyrrole-2-carboxylate, benzyl N-(1-S-carboethoxy-3-cyclopentylpropyl-S-alanyl-(2S,3aS,6aS)-octahydrocyclopenta[b]pyrrole-2-carboxylate, benzyl N-(1-S-carboethoxy-3-phenylpropyl)-S-alanyl-(2S,3aR,6aR)-octahydrocyclopenta[b]pyrrole-2-carboxylate, benzyl N-(1-S-carboethoxy-3-cyclohexylpropyl)-S-alanyl-(2S,3aR,6aR)-octahydrocyclopenta[b]pyrrole-2-carboxylate, tert.-benzyl N-(1-S-carboethoxy-3-phenylpropyl)-N$_\epsilon$-benzyloxycarbonyl-S-lysyl-(2S,3aR,6aR)-octahydrocyclopenta[b]pyrrole-2-carboxylate, benzyl N-(1-S-carboethoxy-3-phenylpropyl)-S-alanyl-(2S,3aS,6aS)-octahydrocyclopenta[b]pyrrole-2-carboxylate, benzyl N-(1-S-carboethoxy-3-cyclohexylpropyl)-S-alanyl-(2S,3aR,6aS)-octahydrocyclopenta[b]pyrrole-2-carboxylate, tert.-butyl N-(1-S-carboethoxy-3-phenylpropyl)-N$_\epsilon$-benzyloxycarbonyl-S-lysyl-(2S,3aR,6aS)-octahydrocyclopenta[b]pyrrole-2-carboxylate, tert.-butyl N-(1-S-carboethoxy-3-cyclohexylpropyl)-N$_\epsilon$-benzyloxycarbonyl-S-lysyl-(2S,3ar,6aS)-octahydrocyclopenta[b]pyrrole-2-carboxylate, benzyl N-(1-S-carboethoxy-3-phenylpropyl)-O-ethyl-S-tyrosyl-(2S,3aR,6aS)-octahydrocyclopenta[b]pyrrole-2-carboxylate, benzyl N-(1-S-carboethoxy-3-cyclopentylpropyl)-S-alanyl-2-alanyl-(2S,3aR,6aS)-octahydrocyclopenta[b]pyrrole-2-carboxylate, benzyl N-(1-S-carboethoxy-3-phenylpropyl)-S-alanyl-S-2-azabicyclo[2.2.2]octane-3-carboxylate, benzyl N-(1-S-carboethoxy-3-phenylpropyl)-O-ethyl-S-tyrosyl-S-2-azabicyclo[2.2.2]octane-3-carboxylate, benzyl N-(1-S-carboethoxy-3-cyclohexylpropyl)-S-alanyl-S-azabicyclo[2.2.2]octane-3-carboxylate, tert.-butyl N-(1-S-carboethoxy-3-cyclohexylpropyl)-N$_\epsilon$-benzyloxycarbonyl-S-2-azabicyclo[2.2.2]octane-3-carboxylate, tert.-butyl N-(1-S-carboethoxy-3-phenylpropyl)-N$_\epsilon$-benzyloxycarbonyl-S-lysyl-S-2-azabicyclo[2.2.2]octane-3-carboxylate, benzyl N-(1-S-carboethoxy-3-cyclopentylpropyl)-S-alanyl-S-2-azabicyclo[2.2.2]octane-3-carboxylate, benzyl N-(1-S-carboethoxy-3-phenylpropyl)-S-alanyl-3S-exo-2-azabicyclo[2.2.1]heptane-3-carboxylate, benzyl N-(1-S-carboethoxy-3-cyclohexylpropyl)-S-alanyl-3S-exo-2-azabicyclo[2.2.1]heptane-3-carboxylate, tert.-butyl N-(1-S-carboethoxy-3-phenylpropyl)-N$_\epsilon$-benzyloxycarbonyl-S-lysyl-3S-exo-2-azabicyclo[2.2.1]heptane-3-carboxylate, benzyl N-(1-S-carboethoxy-3-phenylpropyl)-S-alanyl-3S-endo-2-azabicyclo[2.2.1]heptane-3-carboxylate, benzyl N-(1-S-carboethoxy-3-cyclohexylpropyl)-S-alanyl-3S-endo-2-azabicyclo[2.2.1]heptane-3-carboxylate, tert.-butyl N-(1-S-carboethoxy-3-phenylpropyl)-N$_\epsilon$-benzyloxycarbonyl-S-lysyl-3S-endo-2-azabicyclo[2.2.1]heptane-3-carboxylate, butyl N-(1-S-carboethoxy-3-phenylpropyl)-O-ethyl-S-tyrosyl-3S-endo-2-azabicyclo[2.2.1]heptane-3-carboxylate, benzyl N-(1-S-carboethoxy-3-phenylpropyl)-S-alanyl-2-azaspiro[4.5]decane-3-S-carboxylate, benzyl N-(1-S-carboethoxy-3-phenylpropyl)-O-ethyl-S-tyrosyl-2-azaspiro[4.5]decane-3-S-carboxylate, tert.-butyl N-(1-S-carboethoxy-3-phenylpropyl)-N$_\epsilon$-benzyloxycarbonyl-S-lysyl-2-azaspiro[4.5]decane-3-S-carboxylate, benzyl N-(1-S-carboethoxy-3-cyclohexylpropyl)-S-alanyl-2-azaspiro[4.5]decane-3-S-carboxylate, tert.-butyl N-(1-S-carboethoxy-3-cyclohexylpropyl)-N$_\epsilon$-benzyloxycarbonyl-S-lysyl-2-azaspiro[4.5]decane-3-S-carboxylate, benzyl N-(1-S-carboethoxy-3-phenylpropyl)-S-alanyl-2-azaspiro[4.4]nonane-3-S-carboxylate, benzyl N-(1-S-carboethoxy-3-phenylpropyl)-O-ethyl-S-tyrosyl-2-azabicyclo[4.4]nonane-3-S-carboxylate, benzyl N-(1-S-carboethoxy-3-phenylpropyl)-S-alanylspiro[bicyclo[2.2.1]heptane-2,3'-pyrrolidine]-5'-S-carboxylate, benzyl N-(1-S-carboethoxy-3-phenylpropyl)-O-ethyl-S-tyrosylspiro[bicyclo[2.2.1]heptane-2,3'-pyrrolidine]-5'-S-carboxylate, tert.-butyl N-(1-S-carboethoxy-3-phenylpropyl)-N$_\epsilon$-benzyloxycarbonyl-S-lysylspiro[bicyclo[2.2.1]heptane-2,3'-pyrrolidine]-5'-S-carboxylate, benzyl N-(1-S-carboethoxy-3-cyclohexylpropyl)-S-alanylspiro[bicyclo[2.2.1]heptane-2,3'-pyrrolidine]-5'-S-carboxylate, benzyl N-(1-S-carboethoxy-3-cyclohexylpropyl)-N$_\epsilon$-tert.-butoxycarbonyl-S-lysylspiro[bicyclo[2.2.1]heptane-2,3'-pyrrolidine]-5'-S-carboxylate, benzyl N-(1-S-carboethoxy-3-phenylpropyl)-S-alanylspiro[bicyclo[2.2.2]octane-2,3'-pyrrolidine]-5'-S-carboxylate, benzyl N-(1-S-carboethoxy-3-phenylpropyl)-O-ethyl-S-tyrosylspiro[bicyclo[2.2.1]-octane-2,3'-pyrrolidine]-5'-S-carboxylate, benzyl N-(1-S-carboethoxy-3-phenylpropyl)-N$_\epsilon$-tert.-butoxycarbonyl-S-lysylspiro[bicyclo[2.2.2]octane-2,3'-pyrrolidine]-5'-S-carboxylate, benzyl N-(1-S-carboethoxy-3-cyclohexylpropyl)-S-alanylspiro[bicyclo[2.2.2]octane-2,3'-pyrrolidine]-5'-S-carboxylate, benzyl N-(1-S-carboethoxy-3-phenylpropyl)-S-alanylazatricyclo[4.3.0.1$^{6,9}$]decane-3-S-carboxylate, benzyl N-(1-S-carboethoxy-3-phenylpropyl)-O-ethyl-S-tyrosyl-2-azatricyclo[4.3.0.1$^{6,9}$]decane-3-S-carboxylate, tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate, benzyl N-(1-S-carboethoxy-3-cyclohexylpropyl)-S-alanyl-2-azatricyclo[4.3.0.1$^{6,9}$]-decane-3-S-carboxylate, tert.-butyl N-(1-S-carboethoxy-3-phenylpropyl)-N$_\epsilon$-benzyloxycarbonyl-S-lysyl-2-azatricyclo[4.3.0.1$^{6,9}$]decane-3-S-carboxylate, benzyl N-(1-S-carboethoxy-3-phenylpropyl)-S-alanyldecahydrocyclohepta[b]pyrrole-2-S-carboxylate, benzyl N-(1-S-carboethoxy-3-phenylpropyl)-O-ethyl-S-tyrosyl-decahydrocyclohepta[b]pyrrole-2-S-carboxylate, tert.-butyl N-(1-S-carboethoxy-3-phenylpropyl)-N$_\epsilon$-benzyloxycarbonyl-S-lysyldecahydrocyclohepta[b]pyrrole-2-S-carboxylate, benzyl N-(1-S-carboethoxy-3-cyclohexylpropyl)-S-alanyldecahydrocyclohepta[b]pyrrol-2-S-carboxylate, tert.-butyl N-(1-S-carboethoxy-3-cyclohexylpropyl)-N$_\epsilon$-tert.-butoxycarbonyl-S-lysyldecahydrocyclohepta[b]pyrrole-2-S-carboxylate, benzyl N-(1-S-carboethoxy-3-phenylpropyl)-S-alanyl-transoctahydroisoindole-1-S-carboxylate, benzyl N-(1-S-carboethoxy-3-phenylpropyl)-S-alanyl-cis-octahydroisoindole-1-S-carboxylate, benzyl N-(1-S-carboethoxy-3-cyclohexylpropyl)-S-alanyl-trans-octahydroisoindole-1-S-carboxylate, benzyl N-(1-S-carboethoxy-3-cyclohexylpropyl)-S-alanyl-cis-octahydroisoindole-1-S-carboxylate, benzyl N-(1-S-carboethoxy-3-phenylpropyl)-S-alanyl-cis-octahydrocyclopenta[c]pyrrole-1-S-carboxylate, benzyl N-(1-S-carboethoxy-3-cyclohexylpropyl)-S-alanyl-cis-octahydrocyclopenta[c]pyrrole-1-S-carboxylate, benzyl N-(1-S-carboethoxy-3-cyclohexylpropyl)-N$_\epsilon$-tert.-butoxycarbonyl-S-lysyl-cis-octahydrocyclopenta[c]pyrrole-1-S-carboxylate, benzyl N-(1-S-carboethoxy-3-cyclohexylpropyl)-S-alanyl-cis-octahydrocyclopenta[c]pyrrole-1-S-carboxylate, tert.-butyl N-(1-S-carboethoxy-3-phenylpropyl)-S-alanyl-2,3,3a,4,5,7a-hexahydroindole-2-S-carboxylate, tert.-butyl N-(1-S-carboethoxy-3-phenylpropyl)-O-ethyl-S-tyrosyl-2,3,3a,4,5,7a-hexahydroindole-2-S-carboxylate, tert.-butyl N-(1-S-carboethoxy-3-phenylpropyl)-S-alanylthiazolidine-5-S-carboxylate, tert.-butyl N-(1-S-carboethoxy-3-cyclohexylpropyl)-S-alanylthiazolidine-5-S-carboxylate, tert.-butyl N-(1-S-carboethoxy-3-phenylpropyl)-N$_\epsilon$-benzyloxycarbonyllysylthiazolidine-5-S-carboxylate.

On using precursors which are racemic at the carbon atom bearing the trifluoromethanesulfonate, the N-alkyldipeptides having the R,S configuration in the N-alkyl moiety are obtained.

We claim:

1. A process for the preparation of compounds of the formula I

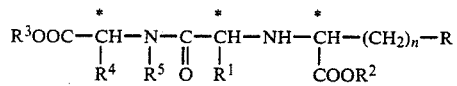

in which n is 1 or 2,

R denotes hydrogen, an aliphatic radical having 1 to 8 carbon atoms, a cycloaliphatic radical having 3-9 carbon atoms, an aromatic radical having 6-12 carbon atoms, an araliphatic radical having 7-14 carbon atoms, a cycloaliphatic-aliphatic radical having 7-14 carbon atoms, or a radical OR$^a$ or SR$^a$, in which R$^a$ represents an aliphatic radical having 1-4 carbon atoms, an aromatic radical having 6-12 carbon atoms or a heteroaromatic radical having 5-12 ring atoms, R$^1$ denotes hydrogen, an aliphatic radical having 1 to 6 carbon atoms, a cycloaliphatic radical having 3-9 carbon atoms, a cycloaliphatic-aliphatic radical having 4-13 carbon atoms, an aromatic radical having 6-12 carbon atoms, an araliphatic radical having 7-16 carbon atoms, a heteroaromatic radical having 5-12 ring atoms, the side-chain of naturally occurring α-aminoacid, or the side-chain of such an amino acid which is protected R$^2$ and R$^3$ are identical or different and denote hydrogen, an aliphatic radical having 1-6 carbon atoms, a cycloaliphatic radical having 3-9 carbon atoms, an aromatic radical having 6-12 carbon atoms, an araliphatic radical having 7-16 carbon atoms, and R$^4$ and R$^5$, together with the atoms carrying them, form a monocyclic, bicyclic or tricyclic heterocyclic ring system having 5 to 15 carbon atoms, which comprises reacting a compound of the formula II

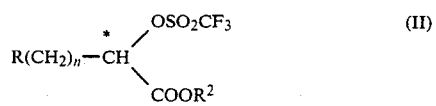

in which n, R, and R$^2$ have the abovementioned meanings, with a compound of the formula IV

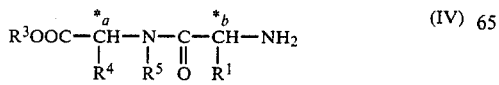

in which R$^1$, R$^3$, R$^4$ and R$^5$ have the above-mentioned meanings, splitting off.

2. The process of claim 1 comprising the further step of saponifying the products of said reaction.

3. The process of claim 1 comprising the further step of esterifying the products of said reaction.

4. The process as claimed in claim 1 in which is prepared a compound of the formula I in which R$^4$ and R$^5$, together with the atoms carrying them, represent a substituted or unsubstituted system from the series comprising pyrrolidine, piperidine, tetrahydroisoquinoline, decahydroisoquinoline, octahydroindole, octahydrocyclopenta[b]pyrrole, 2-azabicyclo[2.2.2]octane, 2-azabicyclo[2.2.1]heptane, 2-azaspiro[4.5]decane, 2-azaspiro[4.4]nonane, spiro[(bicyclo[2.2.1]heptane)-2,3-pyrrolidine], spiro[(bicyclo[2.2.2]octane)-2,3-pyrrolidine], 2-azatricyclo[4.3.0.1$^{6,9}$]decane, decahydrocyclohepta[b]pyrrole, octahydroisoindole, octahydrocyclopenta[c]pyrrole, 2,3,3a,4,5,7a-hexahydroindole or tetrahydrothiazole.

5. The process as claimed in claim 1 in which is prepared a compound of the formula I in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms which can be monosubstituted, disubstituted or trisubstituted by (C$_1$-C$_4$)-alkyl, (C$_1$-C$_4$)-alkoxy, hydroxyl, halogen, nitro, amino, aminomethyl, (C$_1$-C$_4$)-alkylamino, di-(C$_1$-C$_4$)-alkylamino, (C$_1$-C$_4$)-acylamino, preferably (C$_1$-C$_4$)-alkanoylamino, methylenedioxy, carboxyl, cyano and/or sulfamoyl, or alkoxy having 1-4 carbon atoms or aryloxy having 6-12 carbon atoms which can be substituted as described above for aryl, or monocyclic or bicyclic heteroaryloxy having 5-7 or 8-10 ring atoms respectively, 1 to 2 of these ring atoms being sulfur or oxygen atoms and/or 1 to 4 of these ring atoms being nitrogen, which can be substituted as described above for aryl, amino-(C$_1$-C$_4$)-alkyl, (C$_1$-C$_4$)-alkanoylamino-(C$_1$-C$_4$)-alkyl, (C$_7$-C$_{13}$)-aroylamino-(C$_1$-C$_4$)-alkyl, (C$_1$-C$_4$)-alkoxycarbonylamino-(C$_1$-C$_4$)-alkyl, (C$_6$-C$_{12}$)-aryl-(C$_1$-C$_4$)-alkoxycarbonylamino-(C$_1$-C$_4$)-alkyl, (C$_6$-C$_{12}$)-aryl-(C$_1$-C$_4$)-alkylamino-(C$_1$-C$_4$)-alkyl, (C$_1$-C$_4$)-alkylamino-(C$_1$-C$_4$)-alkyl, di-(C$_1$-C$_4$)-alkylamino-(C$_1$-C$_4$)-alkyl, guanidino-(C$_1$-C$_4$)-alkyl, imidazolyl, indolyl, (C$_1$-C$_4$)-alkylthio, (C$_1$-C$_4$)-alkylthio-(C$_1$-C$_4$)-alkyl, (C$_6$-C$_{12}$)-arylthio-(C$_1$-C$_4$)-alkyl, which can be substituted in the aryl moiety as described above for aryl, (C$_6$-C$_{12}$)-aryl-(C$_1$-C$_4$)-alkylthio, which can be substituted in the aryl moiety as described above for aryl, carboxyl-(C$_1$-C$_4$)-alkyl, carboxyl, carbamoyl, carbamoyl-(C$_1$-C$_4$)-alkyl, (C$_1$-C$_4$)-alkoxycarbonyl-(C$_1$-C$_4$)-alkyl, (C$_6$-C$_{12}$)-aryloxy-(C$_1$-C$_4$)-alkyl, which can be substituted in the aryl moiety as described above for aryl, or (C$_6$-C$_{12}$)-aryl-(C$_1$-C$_4$)-alkoxy, which can be substituted in the aryl moiety as described above for aryl, R$^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, (C$_3$-C$_9$)-cycloalkyl-(C$_1$-C$_4$)-alkyl, (C$_5$-C$_9$)-cycloalkenyl-(C$_1$-C$_4$)-alkyl, optionally partially hydrogenated aryl having 6-12 carbon atoms which can be substituted as described above for R, ($C_6$–$C_{12}$)-aryl-($C_1$–$C_4$)-alkyl or ($C_7$–$C_{13}$)-aroyl-($C_1$ or $C_2$)-alkyl, both of which can be substituted as the previous aryl, monocyclic or bicyclic, optionally partially hydrogenated, heteroaryl having 5–7 or 8–10 ring atoms respectively, 1 or 2 of these ring atoms being sulfur or oxygen atoms and/or 1 to 4 of these ring atoms being nitrogen atoms, which can be substituted as the previous aryl, the side chain of a naturally occurring α-aminoacid $R^1$—CH(NH$_2$)—COOH, or the side chain of such an amino acid which is protected, $R^2$ and $R^3$ are identical or different and denote hydrogen, alkyl having 1–6 carbon atoms, alkenyl having 2–6 carbon atoms, di-($C_1$–$C_4$)-alkylamino-($C_1$–$C_4$)-alkyl, ($C_1$–$C_5$)-alkanoyloxy-($C_1$–$C_4$)-alkyl, ($C_1$–$C_6$)-alkoxycarbonyloxy-($C_1$–$C_4$)-alkyl, ($C_7$–$C_{13}$)-aroyloxy-($C_1$–$C_4$)-alkyl, ($C_6$–$C_{12}$)-aryloxycarbonyloxy-($C_1$–$C_4$)-alkyl, aryl having 6–12 carbon atoms, ($C_6$–$C_{12}$)-aryl-($C_1$–$C_4$)-alkyl, ($C_3$–$C_9$)-cycloalkyl or ($C_3$–$C_9$)-cycloalkyl-($C_1$–$C_4$)-alkyl, and $R^4$ and $R^5$ have the meanings indicated above.

6. The process as claimed in claim 1 in which is prepared a compound of the formula I in which
n is 1 or 2, R denotes ($C_1$ to $C_6$)-alkyl, ($C_2$ to $C_6$)-alkenyl, ($C_3$ to $C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$)-alkyl, ($C_6$ to $C_{12}$)-aryl-($C_1$–$C_4$)-alkoxycarbonylamino-($C_1$–$C_4$)-alkyl, ($C_6$ to $C_{12}$)-aryl which can be monosubstituted, disubstituted or trisubstituted by ($C_1$ to $C_4$)-Alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl, $R^1$ denotes hydrogen or ($C_1$ to $C_6$)-alkyl, ($C_1$ to $C_6$)-alkyl substituted by amino, ($C_1$ to $C_6$)-acylamino or benzoylamino, ($C_2$ to $C_6$)-alkenyl, ($C_3$ to $C_9$)-cycloalkyl, ($C_5$ to $C_9$)-cycloalkenyl, ($C_3$ to $C_7$)-cycloalkyl-($C_1$ to $C_4$)-alkyl, ($C_6$ to $C_{12}$)-aryl or partially hydrogenated aryl, each of which can be substituted by ($C_1$ to $C_4$)-alkyl, ($C_1$ or $C_2$)-alkoxy or halogen, ($C_6$–$C_{12}$)-aryl-($C_1$ to $C_4$)-alkyl or ($C_7$–$C_{13}$)-aroyl-($C_1$–$C_2$)-alkyl, both of which can be substituted in the aroyl radical as previously defined, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, a side chain of a naturally occurring α-aminoacid, or the side chain of such an amino acid which is protected, $R^2$ and $R^3$ denote identical or different radicals, hydrogen, ($C_1$ to $C_6$)-alkyl, ($C_2$ to $C_6$)-alkenyl or ($C_6$ to $C_{12}$)-aryl-($C_1$ to $C_4$)-alkyl, and $R^4$ and $R^5$ have the meanings indicated above.

7. The process as claimed in claim 1 in which is prepared a compound of the formula I in which
n is 1 or 2, R denotes methyl, ethyl, cyclohexyl, tert.-butoxycarbonylamino-($C_1$–$C_4$)-alkyl or phenyl which can be monosubstituted or disubstituted or, in the case of methoxy, trisubstituted by phenyl, ($C_1$ to $C_2$)-alkyl, ($C_1$ or $C_2$)-alkoxy, hydroxyl, fluorine, chlorine, bromine, amino, ($C_1$ to $C_4$)-alkylamino, di-($C_1$ to $C_4$)-alkylamino, nitro and/or methylenedioxy, $R^1$ denotes hydrogen, ($C_1$ to $C_3$)-alkyl, ($C_2$ or $C_3$)-alkenyl, the side chain of lysine, the protected side chain of lysine, benzyl, 4-methoxybenzyl, 4-ethoxybenzyl, phenethyl, 4-aminobutyl or benzoylmethyl, $R^2$ and $R^3$ denote identical or different radicals hydrogen, ($C_1$ to $C_4$)-alkyl or benzyl and $R^4$ and $R^5$ have the meanings indicated above.

8. A process for the preparation of compounds of the formula I

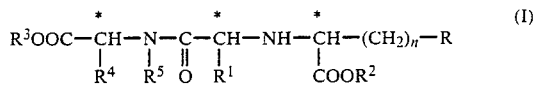

in which
n is 1 or 2,

R denotes hydrogen, an aliphatic radical having 1 to 8 carbon atoms, a cycloaliphatic radical having 3–9 carbon atoms, an aromatic radical having 6–12 carbon atoms, an araliphatic radical having 7–14 carbon atoms, a cycloaliphatic-aliphatic radical having 7–14 carbon atoms, or a radical $OR^a$ or $SR^a$, in which $R^a$ represents an aliphatic radical having 1–4 carbon atoms, an aromatic radical having 6–12 carbon atoms or a heteroaromatic radical having 5–12 ring atoms, $R^1$ denotes hydrogen, an aliphatic radical having 1 to 6 carbon atoms, a cycloaliphatic radical having 3–9 carbon atoms, a cycloaliphatic-aliphatic radical having 4–13 carbon atoms, an aromatic radical having 6–12 carbon atoms, an araliphatic radical having 7–16 carbon atoms, a heteroaromatic radical having 5–12 ring atoms, the side-chain of a naturally occurring α-aminoacid, or the side chain of such an amino acid which is protected $R^2$ and $R^3$ are identical or different and denote hydrogen, an aliphatic radical having 1–6 carbon atoms, a cycloaliphatic radical having 3–9 carbon atoms, an aromatic radical having 6–12 carbon atoms, an araliphatic radical having 7–16 carbon atoms, and $R^4$ and $R^5$, together with the atoms carrying them, form a monocyclic, bicyclic or tricyclic heterocyclic ring system having 5 to 15 carbon atoms, which comprises reacting a compound of the formula III

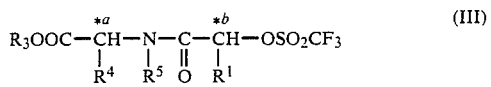

in which $R^1$, $R^3$, $R^4$ and $R^5$ have the above-mentioned meanings, with a compound of the formula V

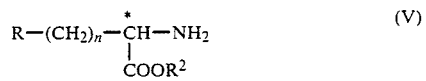

in which n, R and $R^2$ have the above-mentioned meanings.

9. The process of claim 8 comprising the further step of saponifying the products of said reaction.

10. The process of claim 8 comprising the further step of esterifying the products of said reaction.

11. The process as claimed in claim 6 in which is prepared a compound of the formula I in which $R^4$ and $R^5$, together with the atoms carrying them, represent a substituted or unsubstituted system from the series comprising pyrrolidone, piperidine, tetrahydroisoquinoline, decahydroisoquinoline, octahydroindole, octahydrocyclopenta[b]pyrrole, 2-azabicyclo[2.2.2]octane, 2-azabicyclo[2.2.1]heptane, 2-azaspiro[4.5]decane, 2-azaspiro[4.4]nonane, spiro[(bicyclo[2.2.1]heptane)-2,3-pyrrolidine], spiro[(bicyclo[2.2.2]octane)-2,3-pyrrolidine], 2-azatricyclo[4.3.0.1$^{6,9}$]decane, decahydrocyclohepta[b]pyrrole, octahydroisoindole, octahydrocyclopenta[c]pyrrole, 2,3,3a,4,5,7a-hexahydroindole and tetrahydrothiazole.

12. The process as claimed in claim 6 in which is prepared a compound of the formula I in which
n is 1 or 2,
R denotes hydrogen, alkyl having 1–8 carbon atoms, alkenyl having 2–6 carbon atoms, cycloalkyl having 3–9 carbon atoms, aryl having 6–12 carbon atoms which can be monosubstituted, disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-acylamino, preferably $(C_1-C_4)$-alkanoylamino, methylenedioxy, carboxyl, cyano and/or sulfamoyl, or alkoxy having 1–4 carbon atoms or aryloxy having 6–12 carbon atoms which can be substituted as described above for aryl, or monocyclic or bicyclic heteroaryloxy having 5–7 or 8–10 ring atoms respectively, 1 to 2 of these ring atoms being sulfur or oxygen atoms and/or 1 to 4 of these ring atoms being nitrogen, which can be substituted as described above for aryl, amino-$(C_1-C_4)$-alkyl, $(C_1-C_4)$-alkanoylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$-alkyl, $(C_6-C_{12})$-arylthio-$(C_1-C_4)$-alkyl, which can be substituted in the aryl moiety as described above for aryl, $(C_6-C_{12})$-aryl-$(C_1-C_4)$-alkylthio, which can be substituted in the aryl moiety as described above for aryl, carboxyl-$(C_1-C_4)$-alkyl, carboxyl, carbamoyl, carbamoyl-$(C_1-C_4)$-alkyl, $(C_1-C_4)$-alkoxycarbonyl-$(C_1-C_4)$-alkyl, $(C_6-C_{12})$-aryloxy-$(C_1-C_4)$-alkyl, which can be substituted in the aryl moiety as described above for aryl, or $(C_6-C_{12})$-aryl-$(C_1-C_4)$-alkoxy, which can be substituted in the aryl moiety as described above for aryl,
$R^1$ denotes hydrogen, alkyl having 1–6 carbon atoms, alkenyl having 2–6 carbon atoms, alkynyl having 2–6 carbon atoms, cycloalkyl having 3–9 carbon atoms, cycloalkenyl having 5–9 carbon atoms, $(C_3-C_9)$-cycloalkyl-$(C_1-C_4)$-alkyl, $(C_5-C_9)$-cycloalkenyl-$(C_1-C_4)$-alkyl, optionally partially hydrogenated aryl having 6–12 carbon atoms which can be substituted as described above for R, $(C_6-C_{12})$-aryl-$(C_1-C_4)$-alkyl or $(C_7-C_{13})$-aroyl-$(C_1$ or $C_2)$-alkyl, both of which can be substituted as the previous aryl, monocyclic or bicyclic, optionally partially hydrogenated, heteroaryl having 5–7 or 8–10 ring atoms respectively, 1 or 2 of these ring atoms being sulfur or oxygen atoms and/or 1 to 4 of these ring atoms being nitrogen atoms, which can be substituted as the previous aryl, the side chain of a naturally occurring α-aminoacid $R^1$—CH(NH$_2$)—COOH, or the side chain of such an amino acid which is protected,
$R^2$ and $R^3$ are identical or different and denote hydrogen, alkyl having 1–6 carbon atoms, alkenyl having 2–6 carbon atoms, di-$(C_1-C_4)$-alkylamino-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, aryl having 6–12 carbon atoms, $(C_6-C_{12})$-aryl-$(C_1-C_4)$-alkyl, $(C_3-C_9)$-cycloalkyl or $(C_3-C_9)$-cycloalkyl-$(C_1-C_4)$-alkyl, and
$R^4$ and $R^5$ have the meanings indicated above.

13. The process as claimed in claim 6 in which is prepared a compound of the formula I in which
n is 1 or 2,
R denotes $(C_1$ to $C_6)$-alkyl, $(C_2$ to $C_6)$-alkenyl, $(C_3$ to $C_9)$-cycloalkyl, amino-$(C_1-C_4)$-alkyl, $(C_2-C_5)$-acylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6$ to $C_{12})$-aryl-$(C_1-C_4)$-alkoxycarbonylamino-$(C_1-C_4)$-alkyl, $(C_6$ to $C_{12})$-aryl which can be monosubstituted, disubstituted or trisubstituted by $(C_1$ to $C_4)$-Alkyl, $(C_1$ to $C_4)$-alkoxy, hydroxyl, halogen, nitro, amino, $(C_1$ to $C_4)$-alkylamino, di-$(C_1$ to $C_4)$-alkylamino and/or methylenedioxy, or 3-indolyl,
$R^1$ denotes hydrogen or $(C_1$ to $C_6)$-alkyl, $(C_1-C_6)$-alkyl be substituted by amino, $(C_1$ to $C_6)$-acylamino or benzoylamino, $(C_2$ to $C_6)$-alkenyl, $(C_3$ to $C_9)$-cycloalkyl, $(C_5$ to $C_9)$-cycloalkenyl, $(C_3$ to $C_7)$-cycloalkyl-$(C_1$ to $C_4)$-alkyl, $(C_6$ to $C_{12})$-aryl or partially hydrogenated aryl, each of which can be substituted by $(C_1$ to $C_4)$-alkyl, $(C_1$ or $C_2)$-alkoxy or halogen, $(C_6-C_{12})$-aryl-$(C_1$ to $C_4)$-alkyl or $(C_7-C_{13})$-aroyl-$(C_1-C_2)$-alkyl, both of which can be substituted in the aroyl radical as previously defined, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, a side chain of a naturally occurring α-aminoacid, or the side chain of such an amino acid which is protected,
$R^2$ and $R^3$ denote identical or different radicals, hydrogen, $(C_1$ to $C_6)$-alkyl, $(C_2$ to $C_6)$-alkenyl or $(C_6$ to $C_{12})$-aryl-$(C_1$ to $C_4)$-alkyl, and
$R^4$ and $R^5$ have the meanings indicated above.

14. The process as claimed in claim 6 in which is prepared a compound of the formula I in which
n is 1 or 2,
R denotes methyl, ethyl, cyclohexyl, tert.-butoxycarbonylamino-$(C_1-C_4)$-alkyl or phenyl which can be monosubstituted or disubstituted or, in the case of methoxy, trisubstituted by phenyl, $(C_1$ to $C_2)$-alkyl, $(C_1$ or $C_2)$-alkoxy, hydroxyl, fluorine, chlorine, bromine, amino, $(C_1$ to $C_4)$-alkylamino, di-$(C_1$ to $C_4)$-alkylamino, nitro and/or methylenedioxy,
$R^1$ denotes hydrogen, $(C_1$ to $C_3)$-alkyl, $(C_2$ or $C_3)$-alkenyl, the side chain of lysine, the protected side chain of lysine, benzyl, 4-methoxybenzyl, 4-ethoxybenzyl, phenethyl, 4-aminobutyl or benzoylmethyl,
$R^2$ and $R^3$ denote identical or different radicals hydrogen, $(C_1$ to $C_4)$-alkyl or benzyl and
$R^4$ and $R^5$ have the meanings indicated above.

* * * * *